United States Patent [19]

Niwa et al.

[11] Patent Number: 5,532,137
[45] Date of Patent: Jul. 2, 1996

[54] ANTI-FR-900506 SUBSTANCE ANTIBODIES AND HIGHLY-SENSITIVE ENZYME IMMUNOASSAY METHOD

[75] Inventors: Mineo Niwa, Muko; Kouichi Tamura, Daito; Tsutomu Kaizu, Tsukuba; Masakazu Kobayashi, Ikeda, all of Japan

[73] Assignee: Fujisawa Pharmaceutical Co., Ltd., Osaka, Japan

[21] Appl. No.: 465,934

[22] Filed: Jun. 6, 1996

Related U.S. Application Data

[63] Continuation of Ser. No. 337,206, Nov. 7, 1994, abandoned, which is a continuation of Ser. No. 164,777, Dec. 10, 1993, abandoned, which is a continuation of Ser. No. 928,771, Aug. 17, 1992, abandoned, which is a continuation of Ser. No. 769,486, Oct. 1, 1991, abandoned, which is a continuation of Ser. No. 504,722, Apr. 3, 1990, abandoned, which is a continuation of Ser. No. 198,868, May 26, 1988, abandoned.

[30] Foreign Application Priority Data

Jun. 5, 1987 [JP] Japan .................. 62-141776

[51] Int. Cl.$^6$ .................. C07K 16/00; G01N 33/53; G01N 33/543
[52] U.S. Cl. .................. 435/7.92; 435/7.1; 435/7.9; 435/7.93; 435/28; 435/70.21; 435/172.2; 435/240.27; 435/810; 436/518; 436/548; 436/808; 530/387.1; 530/388.9; 530/391.4; 530/808; 530/809; 530/815; 530/864; 530/868
[58] Field of Search .................. 435/7.1, 7.9, 7.92, 435/7.93, 28, 70.21, 172.2, 240.27, 810; 436/64, 518, 548, 808; 530/387.1, 388.9, 391.1, 391.3, 808, 809, 815, 864, 868

[56] References Cited

FOREIGN PATENT DOCUMENTS 0184162  6/1986  European Pat. Off. .

OTHER PUBLICATIONS

Tamura et al. *Chem Abstracts*, vol. 108, 1988, 48617g, "A Highly Sensitive Method to Assay FK–506 Levels in Plasma".

Oellerich, J. Clin. Chem. Clin. Biochem. vol. 22, 1984, pp. 895–904.

P. J. Marangos et al.: Journal of Neurochemistry vol. 33, pp. 319 to 329 (1979).

G. Köhler, C. Milstein: Nature vol. 256, pp. 495 to 497 (1975).

Tamura et al., Trans. Proc., vol. XIX, No. 5, Suppl 6 pp. 23–29 (1987).

U.S. Ser. No. 08/465,934 filed Jun. 6, 1995 pending.

U.S. Ser. No. 08/379,563 filed Feb. 10, 1995 pending.

Primary Examiner—Mary E. Mosher
Assistant Examiner—Laurie Scheiner
Attorney, Agent, or Firm—Oblon, Spivak, McClelland, Maier & Neustadt

[57] ABSTRACT

Monoclonal or polyclonal antibodies capable of recognizing at least one antigenic determinant located on the FR-900506 compound, are disclosed. FR-900506 is a compound having pharmacological activities such as immunosuppressive activity and antimicrobial activity, and has the following structure:

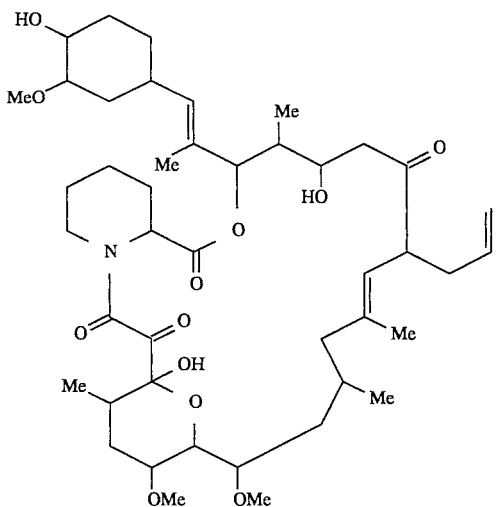

Also disclosed are enzyme immunoassays for FR-900506 based on the antibodies of the invention and test kits for detection of FR-900506. A process for preparing a monoclonal antibody which selectively binds to FR-900506 is also disclosed.

13 Claims, No Drawings

ANTI-FR-900506 SUBSTANCE ANTIBODIES AND HIGHLY-SENSITIVE ENZYME IMMUNOASSAY METHOD

This application is a continuation of application Ser. No. 08/337,206, filed on Nov. 7, 1994, which is a continuation of application Ser. No. 08/164,777, filed on Dec. 10, 1993, which is a continuation of application Ser. No. 07/928,771, filed on Aug. 17, 1992, which is a continuation of application Ser. No. 07/769,486, filed on Oct. 1, 1991, which is a continuation of application Ser. No. 07/504,722, filed on Apr. 3, 1990, which is a continuation of application Ser. No. 07/198,868, filed on May 26, 1988, all now abandoned.

This invention relates to novel antibodies, a highly-sensitive enzyme immunoassay method and a test kit for practicing this method.

More particularly, this invention relates to antibodies capable of recognizing antigenic determinant(s) located on a FR-900506 substance, to a highly-sensitive enzyme immunoassay method, which utilizes an immobilized antibody for the FR-900506 substance (direct method), to a highly-sensitive enzyme immunoassay method for low-molecular weight substances, which comprises the use of a first antibody capable of recognizing a test substance to be assayed and an immobilized second antibody capable of recognizing the said first antibody (indirect method), and to a test kit for measuring the concentration of the FR-900506 substance by the said direct method or indirect method.

The FR-900506 substance is a compound produced by strains of the genus Streptomyces, in particular *Streptomyces tsukubaensis* No. 9993 (deposited at the Fermentation Research Institute,Japan, under the Budapest Treaty route, the deposit number FERM BP-927), which has pharmacological activities such as immunosuppressive activity and antimicrobial activity. It is known that the said compound has the following structural formula (Japanese Kokai Tokkyo Koho JP 61-148181):

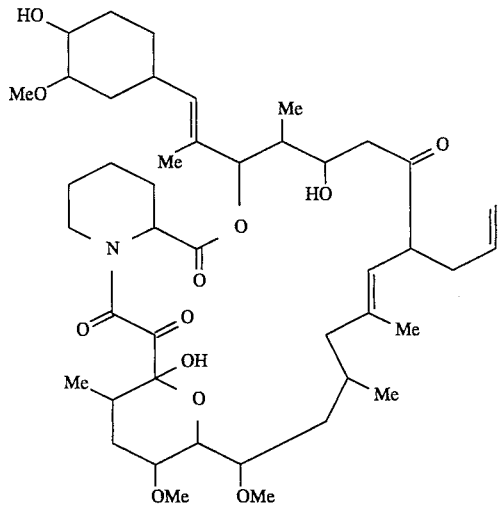

The FR-900506 substance, in very small doses, shows very potent immunosuppressive activity, Therefore, for effectively and continuously suppressing the rejection reaction on the occasion of transplantation, for example organ transplantation, a simple and easy technique is required which will enable highly-sensitive monitoring of the blood concentration of the said compound after administration thereof to living bodies. For such monitoring, to establish a technique for precise determination of very low concentration of the said compound is thought to be of very great importance.

However, any technique of determining very low concentration of the FR-900506 substance in a simple and easy manner and with high sensitivity has not yet been developed . Any antibodies capable of recognizing the FR-900506 substance, and playing an important roll in detecting the FR-900506 substance, have not been developed, either.

The so-far used methods of assaying the small amounts of low-molecular weight substances contained in biological samples and the like include gas chromatography, high-performance liquid chromatography, radioimmunoassay and enzyme immunoassay and so on.

However, these methods are disadvantageous in some sense or other, for example, (1) the sensitivity is insufficient for assaying pharmacologically highly active substances existing in very low concentration, (2) the procedure is complicated, (3) a large-sized apparatus is required and (4) a hazardous radioisotope must be used.

As a result of intensive investigations, the present inventors succeeded in obtaining an antibody capable of recognizing the FR-900506 substance and then they found that the FR-900506 substance existing in very small amounts can be detected in a simple and easy manner with good sensitivity when the said antibody is immobilized, followed by allowing the FR-900506 substance contained in a sample and an enzyme-labeled FR-900506 substance to react competitively with the said antibody.

As a result of further intensive investigations, the present inventors found that the simple, easy and more highly-sensitive assay method for a test substance existing in very small amounts can be provided, when a first antibody capable of recognizing the said test substance and an immobilized second antibody capable of recognizing the said first antibody are used and the test substance contained in a sample and an enzyme-labeled form of the same test substance are allowed to react competitively with the said first antibody. Also,a convenient test kit for practicing the above-mentioned methods was prepared and provided. Based on the above findings, the inventors have now completed the present invention.

The present invention is characterized by four aspects, namely:

(I) An antibody capable of recognizing antigenic determinant(s) located on the FR-900506 substance;

(II) A highly-sensitive enzyme immunoassay method for the FR-900506 substance, which comprises immobilizing an antibody capable of recognizing antigenic determinant(s) located on the FR-900506 substance, allowing the FR-900506 substance contained in a sample and an enzyme-labeled FR-900506 substance to react competitively with the said immobilized antibody and detecting the enzyme-labeled FR-900506 substance bound to the immobilized antibody (direct method);

(III) A highly-sensitive enzyme immunoassay method, which comprises using a first antibody capable of recognizing a test substance to be assayed and an immobilized second antibody capable of recognizing the said first antibody, allowing the test substance contained in a sample and an enzyme-labeled form of the same test substance to react competitively with the said first antibody, and detecting the enzyme-labeled test substance bound to the first antibody bound in turn to the second antibody (indirect method); and (VI) A test kit for the detection of the FR-900506 substance, which comprises an antibody capable of recognizing antigenic determinant(s) located on the FR-900506 substance and an enzyme-labeled form of the FR-900506 substance.

In the following, the present invention is described in further detail.

(I) An antibody capable of recognizing antigenic determinant(s) located on the FR-900506 substance The above-mentioned antibody includes a polyclonal antibody and a monoclonal antibody.

The polyclonal antibody may be classified according to its H chain (heavy chain) into such classes as IgG, IgA, IgM, IgD or IgE and further into subclasses of each class. They may be of any class if they can recognize antigenic determinant(s) located on the FR-900506 substance. A particularly preferred class is IgG, however.

The polyclonal antibody is purified from its antiserum obtained by immunizing an animal with a substance to serve as an immunogen (e.g. the FR-900506 substance).

The immunization step is carried out by a conventional method.

There is no particular limitation as to the animal species to be immunized. Generally, rabbits, guinea pigs, rats, mice, goats and the like are used and, among them, rabbits are particularly preferred.

The substance to serve as immunogen (e.g. the FR-900506 substance) is generally used in the form of a conjugate with a carrier such as bovine serum albumin (hereinafter referred to as BSA), gelatin or hemocyanine so that the immunogenicity can be increased. When the immunogenic substance is the FR-900506 substance, a conjugate with BSA (BSA-FR-900506 substance conjugate) can be obtained, for example, by converting the FR-900506 substance to a half ester of a dicarboxylic acid such as succinic acid, then reacting the half ester with N-hydroxysuccinimide or the like in the presence of a condensing agent such as dicyclohexylcarbodiimide and further reacting the resulting activated ester with BSA.

The polyclonal antibody is purified from the thus-obtained antiserum by conventional means such as salting out with ammonium sulfate or the like, centrifugation, dialysis and column chromatography.

Although the monoclonal antibody may be classified according to its H chain as in the case of polyclonal antibody, any type of monoclonal antibodies can be utilized, as long as it can recognize antigenic determinant(s) located on the FR-900506 substance. A particularly preferred class is IgG, however.

The monoclonal antibody is generally produced by the technique of cell fusion and cloning. It can also be produced by using genetic engineering techniques.

The antibody-producing cells to be used in the step of cell fusion (e.g. anti-FR-900506 substance antibody-producing cells) are, for example, spleen cells, lymph node cells and peripheral lymphocytes of an animal (e.g. mouse, rat, rabbit, goat) immunized with the immunogenic substance having increased immunogenicity (e.g. BSA-FR-900506 substance conjugate). Antibody-producing cells obtained by allowing the immunogen to act, in a culture medium, on the above-mentioned cells or lymphocytes or the like isolated in advance from the unimmunized animals may also be used. When the latter procedure is used, it is also possible to prepare human-derived antibody-producing cells. The antibody-producing cells and myeloma cells, if they are fusible, may be of different animal species origins but is preferably of the same animal species origin.

The monoclonal antibody production using the cell fusion technique is performed by a conventional method, for example by the principal method of Köhler and Milstein [Nature, 256,495 (1975)].

In a particularly preferred embodiment, hybridomas are produced by cell fusion between spleen cells obtained from a mouse immunized with a BSA-FR-900506 substance conjugate and mouse myeloma cells and screened to afford hybridomas producing a monoclonal antibody specific to the FR-900506 substance. The said hybridoma is grown in peritoneal cavities of mice and the monoclonal anti-FR-900506 substance antibody is obtained from the ascitic fluid of the mice.

(II) Enzyme immunoassay for the FR-900506 substance (direct method)

The direct-method is carried out by immobilizing an antibody capable of recognizing antigenic determinant(s) located on the FR-900506 substance, allowing the FR-900506 substance contained in a sample and an enzyme-labeled FR-900506 substance to react competitively with the said immobilized antibody and detecting the enzyme-labeled FR-900506 substance bound to the immobilized antibody. The said antibody capable of recognizing antigenic determinant(s) located on the FR-900506 substance is the one described in the first aspect (I) of the invention. Both of a polyclonal antibody and a monoclonal antibody can be used, but a monoclonal antibody is more preferable because it has a high specificity and there are no differences in their specificities between production lots. Usable as the solid phase for immobilization are, for example, plates (plates for immunological use, etc.), beads (beads for immunological use, etc.), polystyrene balls, and test tubes. From the simple operation viewpoint, immunological plates are preferred. As the enzyme for labeling the FR-900506 substance, there may be mentioned those enzymes which are generally used in various known enzyme immunoassay methods. Thus, usable are, for example, peroxidase, β-D-galactosidase, alkaline phosphatase, glucose oxidase, acetylcholine esterase, glucose-6-phosphate dehydrogenase, malate dehydrogenase and urease. Among them, peroxidase (hereinafter referred to as POD) is a preferred enzyme.

The enzyme-labeled FR-900506 substance can be prepared by a conventional method. Thus, for instance, when a coupling agent is used, the half ester of the FR-900506 substance with a dicarboxylic acid such as succinic acid as described above in illustrating the first aspect (I) of the invention is reacted with N-hydroxysuccinimide or the like and the resultant activated ester of the said half ester is reacted with an enzyme usable for labeling purposes, for example POD.

The enzyme-labeled substance bound to the immobilized antibody is detected by measuring the activity of the enzyme in a conventional manner. When the enzyme used as the label is POD, the POD bound to the immobilized antibody can be assayed by using an enzyme substrate solution of O-phenylenediamine and hydrogen peroxide and measuring the degree of coloration due to oxidation of the substrate as an optical density. The degree of coloration is proportional to the quantity of POD-labeled FR-900506 substance bound to the immobilized antibody.

This direct method can quantitatively and qualitatively assay the FR-900506 substance in very low concentration of $10^{-1}$ to $10^3$ ng/ml in a simple and easy manner.

(III) Enzyme immunoassay (indirect method)

The indirect method is performed by using a first antibody capable of recognizing a test substance to be assayed and an immobilized second antibody capable of recognizing the said first antibody, allowing the test substance contained in a sample and an enzyme-labeled form of the same test substance to react competitively with the said first antibody and detecting the enzyme-labeled test substance bound to the first antibody bound in turn to the second antibody.

The said indirect method can assay various substances, such as peptides, steroids, prostaglandins, polysaccharides and macrocyclic compounds and is particularly useful in concentration determination of macrocyclic compounds, more specifically the FR-900506 substance.

The first antibody may be a polyclonal antibody or a monoclonal antibody provided that it can recognize the test substance, but preferably a monoclonal antibody because it has a high specificity and there are no differences in their specificities between production lots. The said first antibody is prepared in the same manner as described in the first aspect (I) of the invention. When the test substance is the FR-900506 substance, the antibody described above in the first aspect (I) of the invention is useful.

Usable as the second antibody capable of recognizing the said first antibody is an antibody prepared by a conventional method using the first antibody or an antibody of the same species as the first antibody as an immunogen and an antibody which is commercially available as well. Any of them, either polyclonal or monoclonal, can be used provided that it will not interfere with the antigen-antibody reaction between the first antibody and the test substance but can recognize the first antibody. When the first antibody is a class IgG antibody obtained from the rabbit, the use of goat anti-rabbit IgG as the second antibody is preferred. When the first antibody is a class IgG antibody obtained from the mouse, the use of rabbit anti-mouse IgG is preferred.

The solid phase for immobilization, the enzyme for labeling test substances and the method of detecting the said enzyme are the same as those described above in the second aspect (II) of the invention.

When this indirect method is employed, the detection limit for test substances can be varied by adjusting the quantity of the first antibody to be recognized by the immobilized second antibody. Thus, it has been demonstrated that the FR-900506 substance described herein as a typical example of the test substance can quantitatively and qualitatively be assayed down to a very low concentration of the order of 10 ng/ml with high sensitivity and in a simple and easy manner.

(IV) Test kit

This test kit is one for the detection of the FR-900506 substance which comprises an antibody capable of recognizing antigenic determinant(s) located on the FR-900506 substance and an enzyme-labeled FR-900506 substance.

The "antibody capable of recognizing antigenic determinant(S) located on the FR-900506 substance" is either a polyclonal antibody or a monoclonal antibody described above in the first aspect (I) of the invention, but preferably a monoclonal antibody. The said antibody can be supplied in a solid state or in solution.

The "enzyme-labeled FR-900506 substance" is the substance described above in the second aspect (II) of the invention, but preferably a peroxidase-labeled FR-900506 substance.

This substance can also be supplied in a solid state or in solution.

The present test kit may comprises other ingredients usable when practicing the present highly sensitive enzyme immunoassay. For example, it may be a known quantity of FR-900506 substance as a standard for quantitative measurements.

And another is an antibody capable of recognizing "the antibody capable of recognizing antigenic determinant(s) located on the FR-900506 substance" described above in the third aspect (III) of the invention.

And further, another ingredient may be a substrate for the enzyme used as a label for the FR-900506 substance.

EXAMPLE 1

Preparation of polyclonal anti-FR-900506 substance antibody

1) Synthesis of activated ester of FR-900506 substance hemisuccinate

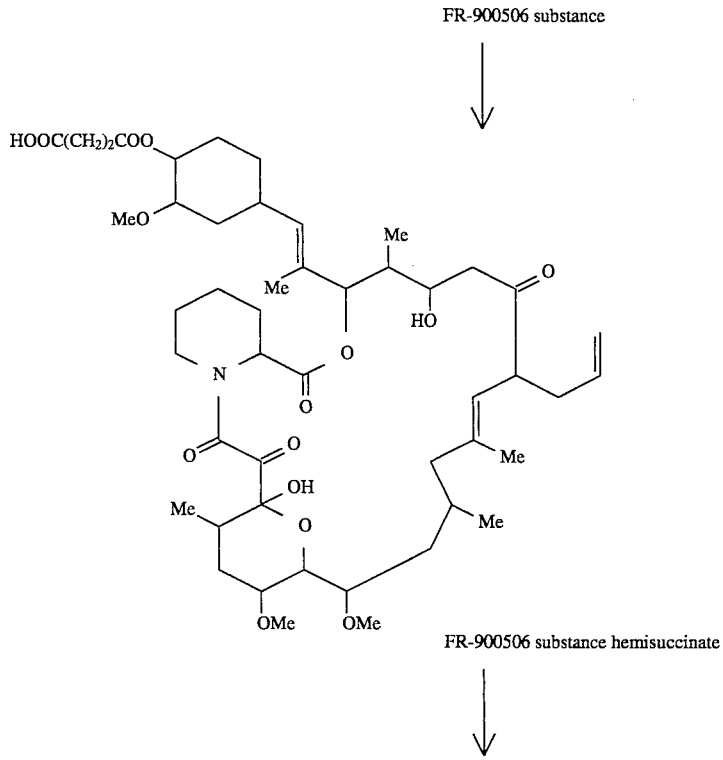

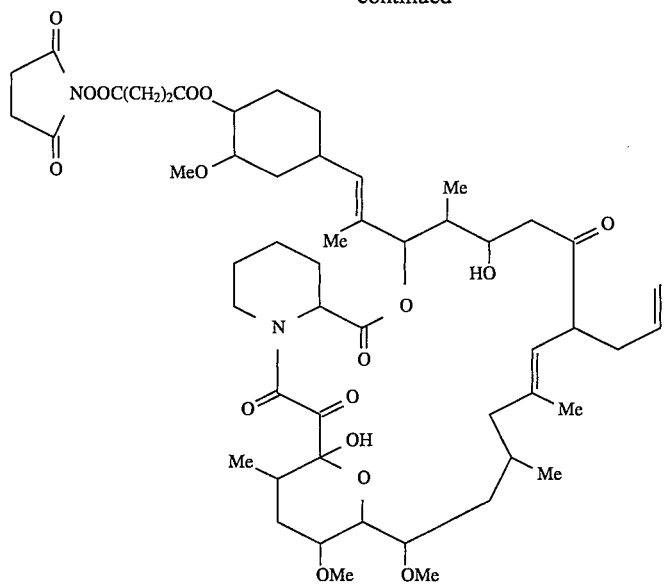

Activated ester of Fr-900506 substance hemisuccinate

The FR-900506 substance (248 mg) was dissolved in pyridine (7 ml). To the solution were added succinic anhydride (145 mg) and 4-dimethylaminopyridine (7 ml). The mixture was stirred at room temperature for 18 hours. The reaction mixture was concentrated to dryness under reduced pressure, and the residue was subjected to silica gel column chromatography. Development with ethyl acetate gave FR-900506 substance hemisuccinate (90 mg). In a solution of this half ester (90 mg) in ethyl acetate (10 ml) was dissolved N-hydroxysuccinimide (12.6 mg), followed by addition of dicyclohexylcarbodiimide (22 mg) with ice cooling. The resulting mixture was stirred overnight at room temperature. The precipitate was filtered off, and the filtrate was evaporated to dryness under reduced pressure. The residue was purified by silica gel thin layer chromatography. Development with ethyl acetate gave the activated ester of the above compound (yield 74.1 mg)

IR v (neat): 1813, 1784, 1735, 1640, 1200 cm$^{-1}$

2) Preparation of BSA-FR-900506 substance conjugate

The activated ester of FR-900506 substance hemisuccinate (37 mg) as obtained in the above manner was dissolved in dioxane (4 ml). To the solution was added a solution of BSA (Armour Pharmaceutical Co.) (30.1 mg) in 0.05 M phosphate buffer (pH 7.3) (10 ml). After 3 days of stirring at 4° C., the reaction mixture was dialyzed against 0.05 M phosphate buffer (pH 7.3) for 24 hours. Thus was prepared a BSA-FR-900506 substance conjugate.

3) Preparation of POD-labeled FR-900506 substance

To a solution of the activated ester of FR-900506 substance hemisuccinate (0.48 mg) as obtained in step 1) in dioxane (10 μl) was added a solution of horseradish peroxidase (Type VI, Sigma Chemical Co.) (10 mg) in dioxane-0.5% sodium hydrogen carbonate (1:1 v/v) solution (0.36 ml), and the resulting mixture was stirred at 4° C. for 2.5 hours. After addition of 0.1% (w/v) gelatin-0.05 M phosphate buffer (pH 7.0) (1.77 ml), the mixture was dialyzed against 0.05 M phosphate buffer (pH 7.0) to give a POD-labeled FR-900506 substance solution.

4) Preparation of polyclonal anti-FR-900506 substance antibody

A solution (2.5 ml) of the BSA-FR-900506 substance conjugate (1.6 mg as BSA) obtained in step 2) in phosphate-buffered physiological saline (hereinafter referred to as PBS) was emulsified in an equal volume of Freund's complete adjuvant, and the emulsion was used to immunize seven female New Zealand white rabbits by injection into the foot pad in a dose of 5 ml and subcutaneous injection in a dose of 5 ml, respectively. After 2 weeks and 3 weeks, supplementary immunizations were made by injection into the foot pad and subcutaneous injection, each in a dose of 5 ml, of an emulsion of the same BSA-FR-900506 conjugate solution in PBS as mentioned above in an equal volume of Freund's incomplete adjuvant.

Three weeks after the second boosting, the final immunization was performed in the same manner. Nine days after the last immunization, exsanguination was performed. To the thus-obtained antiserum (340 ml) were added PBS and 100%-saturated ammonium sulfate, each in an equal volume, for salting out. The resulting precipitate was collected by centrifugation (10,000 rpm×10 minutes), dissolved in 20 mM phosphate buffer (pH 8.0) (200 ml), dialyzed thoroughly against the same buffer (pH 8.0), and purified with DEAE-cellulose column (DE52, Whatman Chemical Separation) equilibrated with the same buffer. A fraction (IgG fraction) which flew through the DEAE-cellulose column and contained a polyclonal anti-FR-900506 substance antibody (5.6 g) was thus obtained (the antibody quantity being calculated based on the absorbance value at the wave length 280 nm).

The solution PBS used in this example was a solution containing, per liter of water, the salts listed below. The same shall apply in the subsequent examples.

| | |
|---|---|
| NaCl | 8.0 g |
| Na$_2$HPO$_4$ | 1.15 g |
| KCl | 0.2 g |
| KH$_2$PO$_4$ | 0.2 g |

EXAMPLE 2

Preparation of monoclonal anti-FR-900506 substance antibody

1) Preparation of monoclonal anti-FR-900506 substance antibody-producing hybridoma A solution of the BSA-FR-900506 substance conjugate obtained in step 2) in Example 1 (50 μg as BSA) in PBS (0.2 ml) was emulsified in an equal volume of Freund's complete adjuvant, and the emulsion was administered to a female BALB/c mouse by intraperitoneal injection. Then, at 2-week intervals, the second and the third immunization (boosting) were conducted each time by intraperitoneal injection of an emulsion of the same amount of the BSA-FR-900506 substance conjugate solution in PBS in an equal volume of Freund's incomplete adjuvant. Thereafter, for the fourth immunization, an emulsion of a ten-fold concentrated PBS solution (0.2 ml) of the BSA-FR-900506 substance conjugate (500 µg as BSA) in Freund's incomplete adjuvant was administered to the mouse by subcutaneous injection.

Further, thereafter, for the last boosting, a solution of the BSA-FR-900506 substance conjugate (200 µg as BSA) in PBS (0.2 ml) was administered to the mouse by intravenous injection into the caudal vein and, after 3 days, the spleen was excised.

This spleen was broken up with forceps, and the spleen cells obtained were fused with mouse myeloma cells (P3× 63Ag8U.1) by the method mentioned below.

Thus, the spleen cells were suspended in Dulbecco's modified Eagle's minimum essential medium (hereinafter referred to as D-MEM). The erythrocytes in the suspension were disrupted by treatment with a mixed solution of 0.83% ammonium chloride solution (9 volumes) and 0.17 M tris(hydroxymethyl)aminomethane hydrochloride buffer (pH 7.65; 1 volume) at 4° C. for 5 minutes and removed by centrifugation. The mouse myeloma cells grown in D-MEM supplemented with 10% of fetal calf serum and the spleen cells were washed several times with D-MEM.

A suspension of the spleen cells (2×10 cells) was added to a suspension of the mouse myeloma cells (4 ×10 cells), and the mixed suspension was shaken well in a 50 ml plastic tube (Corning Glass Work's 50 ml Corning centrifugal tube). The medium was removed by centrifugation, and the cells were warmed to 37° C. on a water bath. A 45% polyethylene glycol (Merck; average molecular weight 4,000) solution (1 ml) was added gradually to the said cells over 1 minute with shaking. The resultant mixture was allowed to stand at room temperature for 5 minutes. The cell fusion reaction was terminated by adding 15 ml of D-MEM dropwise to the reaction mixture over 5 minutes. Then, a large amount of D-MEM was added and the resulting mixture was centrifuged. The supernatant was discarded. To the sediment was added a complete medium (hereinafter referred to as CM) consisting of D-MEM supplemented with 15% fetal calf serum (Centaurus; lot 757), 2 mM glutamine, 2×10 M 2-mercaptoethanol, 100 µg/ml streptomycin sulfate, 100 U/ml penicillin G, 80 µg/ml gentamicin sulfate and Fungizone (amphotericin B; Gibco Laboratories). The mixture was shaken for a while, and the resulting fused cell suspension was distributed into the wells of ten 24-well plates (Nunc) (1 ml(1×10 cells) per well). The cells were incubated at 37° C. in an atmosphere containing 5% carbon dioxide for 1 day. Then, 1 ml of CM containing aminopterine ($4\times10^{-7}$ M), thymidine ($1.6\times10^{-5}$ M) and hypoxanthine ($1\times10^{-4}$ M) (HAT medium) was added to each well. After 1 day, half of the medium was aspirated off from each well and HAT medium was added in compensation therefore. Thereafter, medium exchange was continued at 2- or 3-day intervals.

From among 161 wells in which hybridoma growth was observed, 14 wells of which supernatants showed reactivity to a immobilized BSA-FR-900506 substance conjugate on a solid phase and specific reactivity to the FR-900506 substance were selected. From among the 14 wells, 8 wells of which supernatants showed relatively high antibody titer were further selected and the hybridoma cells therein were cloned by the limiting dilution method using 96-well flat-bottomed microtiter plates (Nunc) with BALB/c mouse thymocytes used as a feeder layer (5×10 cells/ml). Thus were obtained three hybridoma strains capable of producing a monoclonal antibody showing specificity to the FR-900506 substance.

The antibody in each of the above wells was assayed by the method mentioned below so that a clone could be selected when its culture fluid was reactive with the immobilized BSA-FR-900506 substance conjugate on a solid phase mentioned below and at the same time the reaction in question was antagonized by an excess of the FR-900506 substance.

Thus, for confirming the reactivity with the BSA-FR-900506 substance conjugate, the culture fluid (100 µl) was added to each well with a solid phase coat of said conjugate (coating conditions: addition of 100 µl/well of a 20 µg/ml solution in PBS and the subsequent 2 hours of standing at 37° C.) and allowed to stand at 37° C. for 2 hours. After removal of the fluid by aspiration and the subsequent washing, a 2,000-fold dilution (100 µl) of a POD-labeled anti-mouse IgG (Miles; code 61-204.1) [diluent: PBS containing 1% BSA (hereinafter referred to as 1% BSA-PBS)] was added thereto and allowed to stand at 37° C. for 1 hour. After aspiration and washing, the POD activity was measured by a conventional colorimetric method. For judging whether the antibody in question was specifically reactive with the FR-900506 substance, a solution of the FR-900506 substance in 1% BSA-PBS (50 µl) at the concentration of 100 µg/ml was added to each well having a solid phase coat of the BSA-FR-900506 substance conjugate, then the culture fluid (100 µl) was added and, after reaction, the same reaction and coloration procedure with POD-labeled anti-mouse IgG as mentioned above were followed. If the hybridoma culture fluid contained a specific monoclonal antibody against the FR-900506 substance, no coloration would be seen in the presence of excess the FR-900506 substance.

2) Isolation and purification of monoclonal antibody

The three hybridoma strains obtained in step 1) in Example 2 were transplanted into the peritoneal cavities of female BALB/c mice in an immunosuppressed state resulting from administration of 2,6,10,14-tetramethylpentadecane, in a dose of $1\times10^7$ cells per mouse. After 10–14 days, the ascitic fluid was collected and fractionated with 50% saturated ammonium sulfate. The antibody fraction was dialyzed against 10 mM phosphate buffer (pH 8.0) and then subjected to column chromatography on DEAE-cellulose column equilibrated with 10 mM phosphate buffer (pH 8.0). Elution by the linear gradient of sodium chloride (0–150 mM in 10 mM phosphate buffer, pH 8.0) gave fractions of IgG produced by each hybridoma. The subclasses of each IgG were determined by Ouchterlony's double immunodiffusion method (Table 1).

TABLE 1

| Monoclonal antibody | Subclass | Ascitic fluid (ml) | Antibody yield (mg) |
|---|---|---|---|
| FR-900506-1-40-56 | IgG1 | 11 | 125.5 |
| FR-900506-1-53-19 | IgG2b | 6 | 18.7 |
| FR-900506-1-60-46 | IgG1 | 40 | 175.0 |

EXAMPLE 3

Enzyme immunoassay of FR-900506 substance (direct method)

1) Adsorption of antibody onto solid phase

A monoclonal antibody or polyclonal antibody solution (20 µg/ml in PBS) was distributed in 200 µl portions into the wells of ELISA plate S (MS-3496F; Sumitomo Bakelite). After overnight standing at 4° C., the antibody solution was recovered and the plate was washed three time with PBS.

2) Inhibition of nonspecific binding

Each plate treated in the above manner was filled with 1% BSA-PBS and, after 30 minutes of standing at 37° C., the PBS solution was aspirated off.

3) Antigen-antibody reaction (1) Standard FR-900506 substance solutions (diluent: 1% BSA-PBS containing 10% normal serum) were distributed in 100 µl portions into the wells of each plate mentioned above.

(2) A $2 \times 10^5$-fold dilution of the POD-labeled FR-900506 substance solution prepared in step 3) in Example 1 (diluent: 1% BSA-PBS) was distributed in 100 portions into the wells.

(3) The contents of each well were stirred with a plate mixer for 10 seconds and then allowed to stand overnight at 4° C.

4) Enzymatic reaction

Each well was washed twice with PBS containing 0.05% Tween 20 and further twice with PBS. An enzyme substrate solution prepared as described below was distributed 200 µl portions into the wells of each plate and the reaction was allowed to proceed at room temperature for 30 minutes. The enzyme substrate solution was prepared just prior to use.

Enzyme substrate solution:

O-Phenylenediamine (100 mg) and 30% aqueous hydrogen peroxide (50 µl) were dissolved in McIlvaine's buffer (0.1 M disodium hydrogen phosphate adjusted to pH 5.4 by addition of 0.1 M citric acid) (100 ml).

5) Reaction terminating procedure

The reaction was terminated by distributing 4 N sulfuric acid in 50 µl portions into the wells of each plate mentioned above.

6) Measurement

Each reaction mixture was measured for absorbance at the wave length of 492 nm on a Multiskan (trademark, Titertek), with the substrate solution as a control.

The results for the polyclonal anti-FR-900506 substance antibody of Example 1 and the three monoclonal anti-FR-900506 substance antibodies of Example 2 as obtained by following the above assay method using the serum of a normal beagle dog (male) as the normal serum are shown in Table 2.

TABLE 2

Results of enzyme immunoassay of FR-900506 substance by direct method

| Concentration of FR-900506 substance | OD492nm | | | |
| --- | --- | --- | --- | --- |
| (ng/ml) | Po—Ab | Mo–Ab(1) | Mo–Ab(2) | Mo–Ab(3) |
| $10^3$ | 0.019 | 0.022 | 0.015 | — |
| $3.3 \times 10^2$ | 0.070 | 0.067 | 0.038 | 0.006 |
| $1.0 \times 10^2$ | 0.173 | 0.315 | 0.168 | 0.050 |
| $3.3 \times 10$ | 0.258 | 0.500 | 0.375 | 0.090 |
| 10 | 0.385 | 0.879 | 0.512 | 0.256 |
| 3.3 | 0.493 | 0.993 | 0.714 | 0.579 |
| 1 | 0.657 | 0.970 | 0.768 | 0.855 |
| $3.3 \times 10^{-1}$ | 0.747 | 0.952 | 0.782 | 0.916 |
| $1.0 \times 10^{-1}$ | 0.797 | 1.001 | 0.799 | 0.878 |

Po-Ab . . . Polyclonal anti-FR-900506 antibody
Mo–Ab(1) . . . Monoclonal antibody FR-900506-1-40-56
Mo–Ab(2) . . . Monoclonal antibody FR-900506-1-53-19
Mo–Ab(3) . . . Monoclonal antibody FR-900506-1-60-46

EXAMPLE 4

Enzyme immunoassay of FR-900506 substance (indirect method)

1) Adsorption of antibody onto solid phase

A second antibody solution (3 µg/ml, in PBS) was distributed in 200 µl portions into the wells of ELISA plate H (MS-3596F; Sumitomo Bakelite). After overnight standing at 4° C. the antibody solution was recovered, and said plate was washed three times with PBS.

2) Inhibition of nonspecific binding

Each plate treated in the above manner was filled with 1% BSA-PBS (300 µl per well). After 30 minutes of standing at 37° C., the PBS was aspirated off.

3) Antigen-antibody reaction (1) A diluted POD-labeled FR-900506 substance solution (diluent: 1% BSA-PBS; $5 \times 10^4$-fold dilution when the first antibody was a polyclonal antibody; $2 \times 10^5$-fold dilution when the first antibody was a monoclonal antibody) was distributed in 100 µl portions into the wells of each plate mentioned above.

(2) Standard FR-900506 substance solutions (diluent: 1% BSA-PBS containing 10% normal serum) were distributed in 100 µl portions into the wells.

(3) A first antibody solution prepared with 1% BSA-PBS (400 ng/ml when the first antibody was a polyclonal antibody; 10 ng/ml when the first antibody was a monoclonal antibody) was distributed in 50 µl into the wells.

(4) The contents of each well were stirred with a plate mixer for 10 seconds and then allowed to stand overnight at 4° C.

4) Enzymatic reaction

Same as described for step 4) of Example 3.

5) Reaction termination

Same as described for step 5) of Example 3.

6) Measurement

Same as described for step 6) of Example 3.

The results for the polyclonal anti-FR-900506 substance antibody of Example 1 and the monoclonal antibody FR-900506-1-60-46 of Example 2 (each used as the first antibody) as obtained by following the above assay method are shown in Table 3 and Table 4, respectively. The solution of the FR-900506 substance with an appropriate concentration was prepared by dissolving the FR-900506 substance in the normal beagle dog (male) serum.

TABLE 3

Results of enzyme immunoassay of FR-900506 substance by indirect method using polyclonal anti-FR-900506 substance antibody

| Concentration of FR-900506 substance (ng/ml) | OD492nm |
| --- | --- |
| $10^3$ | 0.009 |
| $10^2$ | 0.030 |
| 10 | 0.067 |
| 1 | 0.148 |
| $1 \times 10^{-1}$ | 0.219 |
| $1 \times 10^{-2}$ | 0.262 |
| $1 \times 10^{-3}$ | 0.303 |

TABLE 4

Results of enzyme immunoassay of FR-900506 substance by indirect method using monoclonal anti-FR-900506 substance antibody

| Concentration of FR-900506 substance (ng/ml) | OD492nm |
|---|---|
| 5 | 0.003 |
| 2 | 0.063 |
| 1 | 0.168 |
| $5 \times 10^{-1}$ | 0.359 |
| $2 \times 10^{-1}$ | 0.660 |
| $1 \times 10^{-1}$ | 1.879 |
| $5 \times 10^{-2}$ | 1.088 |
| $2 \times 10^{-2}$ | 1.232 |

The second antibody used was goat anti-rabbit IgG [Miles' antiserum (code 64-331-1) purified by salting out with ammonium sulfate and treatment on DEAE cellulose column] when the first antibody used was the polyclonal anti-FR-900506 substance antibody, and rabbit anti-mouse IgG (EY laboratories; catalog No. AF-011) when the first antibody used was the monoclonal antibody FR-900506-1-60-46.

EXAMPLE 5

Plasma concentration assay by indirect method

A single dose (1 mg/kg) of a solid dispersion formulation of the FR-900506 substance having the composition given below was orally administered to three male beagle dogs, and the plasma concentration was monitored for each animal by following the assay procedure described in Example 4 (the system using the monoclonal antibody FR-900506-1-60-46 as the first antibody) and using a 10-fold dilution of the plasma sample (diluent: 1% BSA-PBS) in lieu of the standard FR-900506 substance solutions diluted with 1% BSA-PBS containing 10% normal serum. The data thus obtained (each mean of three animals) are shown in Table 5. In the table, "time" indicates the time after administration of the FR-900506 substance-containing solid dispersion formulation.

| Composition of solid dispersion formulation (per gram) | |
|---|---|
| FR-900506 substance | 0.2 g |
| Hydroxypropylmethylcellulose 2910 (TC-5R) | 0.2 g |
| Croscarmellose sodium (AC-Di-Sol) | 0.2 g |
| Lactose | 0.4 g |

TABLE 5

Results of monitoring of plasma concentration of The FR-900506 substance by indirect method

| Time (hr) | Concentration of FR-900506 substance (ng/ml) |
|---|---|
| 0.5 | 1.94 |
| 1 | 1.99 |
| 2 | 1.02 |
| 4 | 0.97 |
| 6 | 0.83 |
| 8 | 0.46 |
| 24 | 0.07 |

EXAMPLE 6

A test kit (I) for practicing an indirect method
Kit components (for 1,000 samples)

(1) A first antibody (a monoclonal anti-FR-900506 substance antibody) solution (500 μl)[1]: 1 μg/ml in 1% BSA-PBS
(2) POD-labeled FR-900506 substance solution (500 μl)[2]: A 1,000-fold diluted solution, by 1% BSA-PBS, of the solution prepared in a Step 3) of Example 1.
(3) Standard FR-900506 substance solution (1 ml)[3]: 1 mg/ml in methanol
(4) A second antibody (rabbit anti-mouse IgG) solution (600 μl)[4]: 1 mg/ml in PBS 1) ... it is used after 100-fold dilution by 1%BSA-PBS.
2) ... it is used after 200-fold dilution by 1%BSA-PBS.
3) ... it is used after suitable dilution by 1%BSA-PBS.
4) ... it is used after 333-fold dilution by PBS.

The present test kit is used for practicing a indirect method according to the procedure of Example 4.

EXAMPLE 7

A test kit (II) for practicing an indirect method
[Kit components (for 1,000 samples)]
(1) A first antibody (a monoclonal anti-FR-900506 substance antibody) solution (1 ml)[1]: 1 μg/ml in 1% BSA-PBS
(2) POD-labeled FR-900506 substance solution (700 μl)[2]: A 1,000-fold diluted solution, by 1%BSA-PBS, of the solution prepared in a Step 3) of Example 1.
(3) FR-900506 substance standard solutions (respectively 1 ml) : 100, 50, 20, 10, 5, 2, 1, 0.5, 0.2 and 0 ng/ml in methanol
(4) A second antibody (rabbit anti-mouse IgG) solution (1 ml )[3]: 1 mg/ml in PBS 1) ... it is used after 50-fold dilution by 1%BSA-0.05% Tween 20-PBS.
2) ... it is used after 300-fold dilution by 1%BSA-0.05% Tween 20-PBS.
3) ... it is used after 200-fold dilution by PBS.

The present test kit (II) is used for practicing a indirect method according to the following column route or extraction route.

[Column route]
1. Add 0.1N hydrochloric acid (1.0 ml) and methanol (10 μl) to the plasma or serum sample (100 μl), and stir for several seconds.
1'. Preparation of the FR-900506 substance standard solution
    Add 0.1N hydrochloric acid (1.0 ml) and the respective FR-900506 substance standard solution (10 μl) to normal plasma or serum (100 μl), and stir for several seconds.
2. Column treatment
    i) Conditioning of the column Sep-Pak column (trademark, $C_{18}$ cartledge column, Waters Associates (US)) is activated by washing with 5 ml of methanol, and is washed with 20 ml of 4% aqueous acetic acid, successively.
    ii) Adsorption Apply 1 ml of the sample or the standard solution which is described in the step 1 or 1', over the conditioned Sep-Pak column.
    iii) Washing Wash the Sep-Pak column with 20 ml of 4% aqueous acetic acid.
    iv) Elution Elute the adsorbed FR-900506 substance with 3 ml of methanol, and collect the eluate into a v-shaped bottom test tube.
3. Concentrate the eluate by the stream of dry nitrogen gas 4. Dissolve the residue with 200 µl of POD-labeled FR-900506 substance solution of 1% BSA-0.05% Tween 20-PBS.
5. The second antibody solution (200 µl) is added to each well of a 96-well flat bottom microtiter plate, and the plate is incubated at 4° C. overnight.
6. After incubation, the second antibody solution is removed from the wells by suction.
7. The plate is washed 3 times with PBS.
8. Immediately after the third wash, each well of the plate is filled with 300 µl of 1% BSA-0.05% Tween 20-PBS (the blocking solution).
9. The plate is incubated for 1 hour at room temperature.
10. The blocking solution is aspirated off out of one well, and 180 µl of the sample or the standard obtained in Step 4 is added to the well of the plate, immediately. This replacement of the blocking solution with the sample or the standard should be done well by well until all the samples are added to the appropriate wells.
11. A first antibody solution (50 µl) is added to each well.
12. The plate is incubated overnight on a plate rotator at 4° C.
13. After incubation, the solution is aspirated off, and the plate is washed twice with 0.05% Tween 20-PBS and twice with PBS.
14. Immediately, 200 µl of the substrate solution which is described in the step 4) of Example 3, is added to each well and the plate is incubated at room temperature for 15 minutes.
15. 4N sulfuric acid is added to each well to stop the reaction of POD with hydrogen peroxide and O-phenylenediamine.
16. The optical density at 492 nm ($OD_{492}$) of the sample well is measured, subtracting the OD of the background well.

[Extraction route]
1. Methanol (10 µl), 0.2 M Phosphate buffer (pH 7.0) (1 ml) and dichloromethane (6.0 ml) are added to plasma or serum sample(100 µl)
1'. The respective FR-900506 substance standard solutions (10 µl) is mixed with plasma (100 µl) from normal respective animal species, 0.2 M Phosphate buffer (pH 7.0) (1.0 ml) and dichloromethane (6.0ml).
2. The each mixture is stirred for 10 minutes and centrifuged for 10 minutes at 3000 rpm.
3. The bottom layer of dichloromethane (5.0 ml) is separated out and evaporated to dryness under a stream of dry nitrogen gas.

The dried residue extracts obtained in the step 3 are subsequently treated for indirect method according to similar manners to the Steps 4–16 of the before-mentioned column route.

What we claim is:

1. A monoclonal antibody capable of recognizing antigenic determinant(s) located on the FR-900506 substance, which is prepared by:
    i) performing cell fusion between (a) a spleen cell immunized with a FR-900506 substance conjugate with a suitable carrier which is prepared by reacting the suitable carrier with a hydroxyl group on the cyclohexyl moiety of the FR-900506 substance, and (b) a myeloma cell,
    ii) screening the hybridoma producing a monoclonal antibody specific to the FR-900506 substance, and
    iii) obtaining the monoclonal anti-FR-900506 substance antibody, the class of which is IgG,
    in which the FR-900506 substance conjugate with a suitable carrier is the one made by
        a) converting the FR-900506 substance to a half ester of a dicarboxylic acid,
        b) activating its half ester, and
        c) reacting its activated ester with a suitable carrier which can increase the immunogenicity of the FR-900506 substance,
    in which the FR-900506 substance conjugate with a suitable carrier is the one made by reacting the activated ester of FR-900506 substance hemisuccinate of the following formula:

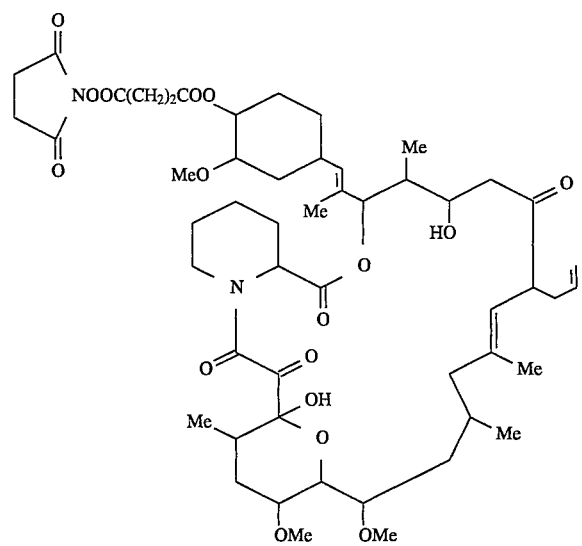

with a carrier selected from bovine serum albumin, gelatin and hemocyanine.

2. The monoclonal antibody of claim 1, which is reactive with the immobilized bovin serum albumin-FR-900506 substance conjugate on a solid phase and at the same time is antagonized by an excess of the FR-900506 substance.

3. A highly-sensitive enzyme immunoassay method for the FR-900506 substance, which comprises immobilizing a monoclonal antibody of claim 1, allowing the FR-900506 substance contained in a sample and an enzyme labeled FR-900506 substance to react competitively with the immobilized antibody and detecting the enzyme-labelled substance bound to the immobilized antibody.

4. A highly-sensitive enzyme immunoassay method as claimed in claim 3, wherein the enzyme is a peroxidase.

5. A highly-sensitive enzyme immunoassay method for measuring the concentration of FR-900506 substance in sample fluids, which is characterized in
    i) using a first monoclonal antibody of claim 1 and a second antibody capable of recognizing the said first monoclonal antibody, wherein said second antibody is immobilized on a plate,
    ii) allowing the FR-900506 substance in a sample and an enzyme-labeled FR-900506 substance to react competitively with the above-mentioned first monoclonal antibody, and
    iii) detecting the enzyme-labeled FR-900506 substance bound to the above-mentioned first monoclonal antibody bound in turn to the second antibody.

6. A highly-sensitive enzyme immunoassay method as claimed in claim 5, wherein the enzyme is a peroxidase.

7. A test kit for the detection of the FR-900506 substance, which comprises a monoclonal anti-FR-900506 substance antibody as claimed in claim 1 and an enzyme-labeled FR-900507 substance.

8. A test kit as claimed in claim 7, which further comprises a know quantity of FR-900506 substance as a standard.

9. A test kit as claimed in claim 7, which further comprises an antibody capable of recognizing a monoclonal anti-FR-900506 substance antibody.

10. A test kit as claimed in claim 7, wherein the enzyme-labeled FR-900506 substance is a peroxidase-labeled FR-900506 substance.

11. A test kit as claimed in claim 10, which further comprises an antibody capable of recognizing a monoclonal anti-FR-900506 substance antibody.

12. A test kit as claimed in claim 10 which further comprises a known quantity of FR-900506 substance as a standard.

13. A test kit as claimed in claim 12 which further comprises an antibody capable of recognizing a monoclonal anti-FR-900506 substance antibody.

\* \* \* \* \*

UNITED STATES PATENT AND TRADEMARK OFFICE
CERTIFICATE OF CORRECTION

PATENT NO. : 5,532,137
DATED: : JULY 2, 1996
INVENTOR(S) : MINEO NIWA, ET AL

It is certified that error appears in the above-identified patent and that said Letters patent is hereby corrected as shown below:

On the Title Page, delete item [22] in its entirety and replace with
--[22] Filed: Jun. 6, 1995--.

Column 7, line 25, "Fr-900506" should read --FR-900506--.

Column 7, line 42, "IR ν (neat):" should read --IR ν (neat):--.

Column 9, line 29, "(2x10 cells)" should read --($2 \times 10^8$ cells)--.

Column 9, line 30, "(4x10 cells)" should read --($4 \times 10^7$ cells)--.

Column 9, line 45, "2x10 M" should read --$2 \times 10^{-5}$ M--.

Column 9, line 51, "(1 ml(1x10 cells)" should read --(1 ml($1 \times 10^6$ cells)--.

Column 10, line 1, "5x10 cells" should read --$5 \times 10^6$ cells--.

Column 11, line 16, "in 100 portions" should read --in $100 \mu l$ portions--.

UNITED STATES PATENT AND TRADEMARK OFFICE
CERTIFICATE OF CORRECTION

PATENT NO. : 5,532,137
DATED : July 2, 1996
INVENTOR(S) : Mineo Niwa, et. al.

It is certified that error appears in the above-identified patent and that said Letters Patent is hereby corrected as shown below:

Column 14, lines 54 and 55, should read as follows:

--i) Conditioning of the column
Sep-Pak column (trademark, $C_{18}$ cartledge column, Waters Associates--;

lines 59 and 60 should read as follows:

--ii) Adsorption
Apply 1 ml of the sample or the standard--;

lines 62 and 63 should read as follows:

--iii) Washing
Wash the Sep-Pak column with 20 ml of--;

lines 64 and 65, should read as follows:

--iv) Elution
Elute the adsorbed FR-900506 substance--.

Column 15, line 36, "OD of the" should read --$OD_{492}$ of the--.

Signed and Sealed this

Thirtieth Day of June, 1998

Attest:

*Attesting Officer*

BRUCE LEHMAN
*Commissioner of Patents and Trademarks*